(12) United States Patent
Kwak et al.

(10) Patent No.: US 12,343,139 B2
(45) Date of Patent: Jul. 1, 2025

(54) SWEAT SENSOR PATCH

(71) Applicants: KOREA INSTITUTE OF SCIENCE AND TECHNOLOGY, Seoul (KR); IUCF-HYU (Industry-University Cooperation Foundation Hanyang University), Seoul (KR)

(72) Inventors: Rhokyun Kwak, Seoul (KR); Jina Choi, Gwangmyeong-si (KR); Sangha Kim, Seoul (KR); Hyunjung Yi, Seoul (KR); Seongjin Park, Seoul (KR)

(73) Assignees: KOREA INSTITUTE OF SCIENCE AND TECHNOLOGY, Seoul (KR); IUCF HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 801 days.

(21) Appl. No.: 17/471,165

(22) Filed: Sep. 10, 2021

(65) Prior Publication Data

US 2023/0013756 A1    Jan. 19, 2023

(30) Foreign Application Priority Data

Jul. 13, 2021    (KR) ........................ 10-2021-0091860

(51) Int. Cl.
*A61B 5/145*    (2006.01)
*A61B 5/00*    (2006.01)
(Continued)

(52) U.S. Cl.
CPC ........ *A61B 5/14517* (2013.01); *A61B 5/1477* (2013.01); *A61B 5/6833* (2013.01); *A61B 10/0064* (2013.01)

(58) Field of Classification Search
CPC .............. A61B 5/14517; A61B 5/1477; A61B 5/6832–6833; A61B 10/0064;
(Continued)

(56) References Cited

U.S. PATENT DOCUMENTS

2018/0249935 A1    9/2018  Rao et al.
2018/0271414 A1*   9/2018  Deck .................... A61B 5/6833
(Continued)

FOREIGN PATENT DOCUMENTS

CN    109374713 B    11/2019
CN    104280444 B    12/2019
(Continued)

OTHER PUBLICATIONS

English Translation of WO 2020225870 A1, Nippon Telegraph and Telephone Corporation, 6 pages, printed on May 15, 2024, (Year: 2020).*

(Continued)

*Primary Examiner* — Devin B Henson
*Assistant Examiner* — Jennifer Grace Baires-Tweed
(74) *Attorney, Agent, or Firm* — CANTOR COLBURN LLP

(57) ABSTRACT

A sweat sensor patch of the present disclosure is a sweat sensor patch attached to a skin of a user and used, and includes: an opening formed layer which has a first surface and a second surface which face in opposite directions, and includes an opening penetrating in a thickness direction from the first surface to the second surface; an electrode layer formed on an inner wall surface of the opening; a porous layer which is stacked on the second surface of the opening formed layer and is formed to cover the opening; and a porous pillar which extends in the thickness direction of the opening formed layer within the opening and is connected with the porous layer.

15 Claims, 18 Drawing Sheets

(51) Int. Cl.
*A61B 5/1477* (2006.01)
*A61B 10/00* (2006.01)

(58) Field of Classification Search
CPC .......... A61B 5/257–259; A61B 5/4261–4266; A61B 2562/12; A61B 2562/164; A61B 2560/0412; A61B 5/14507; A61B 5/25–251; A61B 2562/16; A61M 5/14248; A61N 1/0492
See application file for complete search history.

(56) References Cited

U.S. PATENT DOCUMENTS

| | | | |
|---|---|---|---|
| 2019/0106613 A1 | 4/2019 | Wang et al. | |
| 2020/0187848 A1* | 6/2020 | Han | H10N 30/88 |

FOREIGN PATENT DOCUMENTS

| | | | | |
|---|---|---|---|---|
| CN | 110823968 A | | 2/2020 | |
| CN | 111759359 A | | 10/2020 | |
| EP | 3639743 A1 | | 4/2020 | |
| JP | 2017-80245 A | | 5/2017 | |
| JP | 2020-171350 A | | 10/2020 | |
| KR | 10-1971269 B1 | | 4/2019 | |
| KR | 1020190040610 A | | 4/2019 | |
| KR | 101990894 B1 | | 6/2019 | |
| KR | 20200075719 A | * | 6/2020 | .......... A61B 5/6833 |
| KR | 1020200075719 A | | 6/2020 | |
| KR | 10-2020-0082891 A | | 7/2020 | |
| KR | 102236245 B1 | | 4/2021 | |
| WO | WO-2020225870 A1 | * | 11/2020 | .......... A61B 5/0002 |
| WO | WO-2021063990 A1 | * | 4/2021 | .......... A61M 39/105 |

OTHER PUBLICATIONS

English Translation of KR 20200075719 A, Amore Pacific Co., Ltd., Massachusetts Institute of Technology, 17 pages, printed on May 15, 2024, (Year: 2020).*

* cited by examiner

→ Body fluid passage
---→ Air passage

SWEAT SENSOR PATCH

CROSS-REFERENCE TO RELATED APPLICATION

This application claims priority to and the benefit of Korean Patent Application No. 10-2021-0091860 filed in the Korean Intellectual Property Office on Jul. 13, 2021, the entire contents of which are incorporated herein by reference.

BACKGROUND OF THE INVENTION (a) Field of the Invention

The present disclosure relates to a sweat sensor patch used while being attached to a skin of a user.

(b) Description of the Related Art

With the advent of the Internet of Things era, where things and things or things and people are connected, the role of wearable devices is being emphasized. In line with this trend, wearable devices for measuring the interaction between the body and the external environment are being studied.

Customized technology that measures biometric information non-invasively and long-term, efficiently manages personal health and adopts the measured biometric information to treatment based on the biometric information is in the spotlight as a technology that can change the paradigm of the future medical and health care industry. Recently, in particular, research on a skin attached sensor which is attached to a skin to monitor a bio-signal is also being actively conducted. The bio-signal provides important information for biomedical devices, and multiple biosensors are essentially required to obtain individual signals from multiple points in a wide area.

In recent research, a sensor for the body surface has been developed to acquire bio-signals, such as electromyography and electrocardiogram, in a living body by using an ultra-thin film or an adhesive substrate. However, most of the existing sensors for the body surface have a structure in which a sensor platform covering the skin is blocked.

However, since the human skin is composed of an open system in which water evaporation, sweat secretion, and the like continuously occur, when it is desired to obtain bio-signals for a long time by using a sensor, it is necessary to consider not only the movement of the human body, but also the transepidermal water loss in which water evaporates through the skin or sweating.

When water that needs to be continuously evaporated through the skin is not appropriately discharged due to the sensor attached to the skin, the user may feel uncomfortable due to wearing the sensor for a long time and risks, such as skin itching and skin necrosis, may also follow. Further, the adhesion of a sensor element to the human body is significantly reduced due to water that is not appropriately discharged and remains between the skin and the sensor attached to the skin, thereby causing a side effect of reducing the accuracy of the bio-signal to be measured.

Accordingly, there is a need for a skin-attached sensor capable of overcoming the limitations of the existing skin-attached sensor and capable of controlling breathability and moisture permeability to enable long-term monitoring of multiple bio-signals.

The above information disclosed in this Background section is only for enhancement of understanding of the background of the invention, and therefore it may contain information that does not form the prior art that is already known in this country to a person of ordinary skill in the art.

SUMMARY OF THE INVENTION

The present invention has been made in an effort to provide a sweat sensor patch, in which an air passage and a body fluid passage are structurally separated in a sweating passage to facilitate collection and removal of sweat, thereby continuously acquiring bio-signals of a user for a long time.

However, the object to be solved in the exemplary embodiments of the present invention is not limited to the foregoing object, and may be variously extended in the scope of the technical spirit included in the present invention.

An exemplary embodiment of the present invention provides a sweat sensor patch attached to a skin of a user and used, the sweat sensor patch including: an opening formed layer which has a first surface and a second surface which face in opposite directions, and includes an opening penetrating in a thickness direction from the first surface to the second surface; an electrode layer formed on an inner wall surface of the opening; a porous layer which is stacked on the second surface of the opening formed layer and is formed to cover the opening; and a porous pillar which extends in the thickness direction of the opening formed layer within the opening and is connected with the porous layer.

The porous layer may include a hydrophilic material.

The porous pillar may include a hydrophobic material.

The porous pillar may be positioned while being spaced apart from the inner wall surface of the opening The porous pillar may be fixed to and supported by the porous layer.

The porous pillar may extend so as to penetrate the porous layer from the first surface of the opening formed layer.

The porous pillar may be spaced from the first surface of the opening formed layer, so that one end of the porous pillar is positioned within the opening.

The porous layer and the porous pillar may include a hydrophilic material.

The electrode layer may include a working electrode, and a reference electrode which forms a pair with the working electrode and is electrically connected with the working electrode.

Another exemplary embodiment provides a sweat sensor patch attached to a skin of a user and used, the sweat sensor patch including: an opening formed layer which has a first surface and a second surface which face in opposite directions, and includes an opening penetrating in a thickness direction from the first surface to the second surface; an electrode layer formed on an inner wall surface of the opening; and a porous layer stacked on the second surface of the opening formed layer, and includes an air hole penetrating so as to correspond to the opening.

The porous layer may include a hydrophilic material.

A planar area of the air hole of the porous layer may be smaller than a minimum planar area of the opening of the opening formed layer.

A cross-section of the opening cut in a plane perpendicular to the thickness direction of the opening formed layer may be formed of a polygon having corners.

The cross-section of the opening may have one of a quadrangular shape or a hexagram shape.

The electrode layer may include a working electrode, and a reference electrode which forms a pair with the working electrode and is electrically connected with the working electrode, and the working electrode may be disposed to be adjacent to the reference electrode with one corner of the opening interposed therebetween to form a pair with the reference electrode.

Still another exemplary embodiment provides a sweat sensor patch attached to a skin of a user and used, the sweat sensor patch including: an opening formed layer which has a first surface and a second surface which face in opposite directions, and includes an opening penetrating in a thickness direction from the first surface to the second surface; an electrode layer formed on an inner wall surface of the opening; and a channel formed layer which is stacked on the second surface of the opening formed layer, and includes an air channel passing so as to communicate with the opening and extending in a plane direction of the opening formed layer.

The air channel may extend at least in four directions about the opening in the plane direction of the opening formed layer.

The air channel may be formed in a space between the second surface of the opening formed layer and the channel formed layer.

The channel formed layer may further include a pillar extending in a thickness direction of the channel formed layer from a surface facing the opening formed layer at a position corresponding to the opening.

The channel formed layer may include a hydrophilic material, a hygroscopic material, or hydrogel.

A cross-section of the opening cut in a plane perpendicular to the thickness direction of the opening formed layer may be formed of a polygon having corners.

The electrode layer may include a working electrode, and a reference electrode which forms a pair with the working electrode and is electrically connected with the working electrode, and the working electrode may be disposed to be adjacent to the reference electrode with one corner of the opening interposed therebetween to form a pair with the reference electrode.

According to the sweat sensor patches of the exemplary embodiments, it is possible to implement an air passage and a body fluid passage in one opening at the same time, thereby structurally separating the air passage and the body fluid passage in a path in which sweat is discharged. Accordingly, it is possible to easily collect and remove sweat, thereby continuously acquiring bio-signals of a user for a long time.

DETAILED DESCRIPTION OF THE EMBODIMENTS

Figure 1:
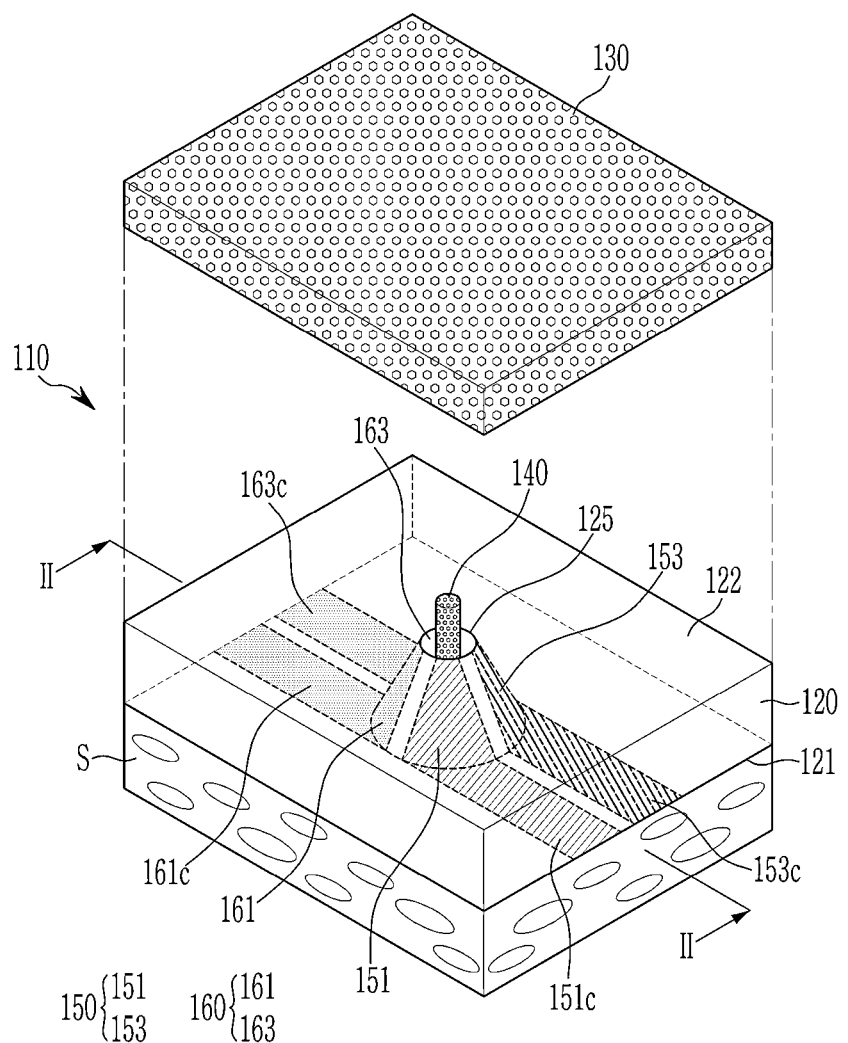
FIG. 1 is an exploded perspective view illustrating a unit structure of a sweat sensor patch according to an exemplary embodiment.

The present invention will be described more fully hereinafter with reference to the accompanying drawings, in which exemplary embodiments of the invention are shown. The drawings and description are to be regarded as illustrative in nature and not restrictive. Like reference numerals designate like elements throughout the specification. Further, some constituent elements in the accompanying drawings are exaggerated, omitted, or schematically illustrated, and a size of each constituent element does not fully reflect an actual size.

Further, the accompanying drawings are provided for helping to easily understand exemplary embodiments disclosed in the present specification, and the technical spirit disclosed in the present specification is not limited by the accompanying drawings, and it will be appreciated that the present invention includes all of the modifications, equivalent matters, and substitutes included in the spirit and the technical scope of the present invention.

Terms including an ordinary number, such as first and second, are used for describing various constituent elements, but the constituent elements are not limited by the terms. The terms are used only to discriminate one constituent element from another constituent element.

Further, it will be understood that when an element such as a layer, film, region, or substrate is referred to as being "on" another element, it can be directly on the other element or intervening elements may also be present. In contrast, when an element is referred to as being "directly on" another element, there are no intervening elements present. Further, when an element is "on" a reference portion, the element is located above or below the reference portion, and it does not necessarily mean that the element is located "on" in a direction opposite to gravity.

In the present application, it will be appreciated that terms "including" and "having" are intended to designate the existence of characteristics, numbers, steps, operations, constituent elements, and components described in the specification or a combination thereof, and do not exclude a possibility of the existence or addition of one or more other characteristics, numbers, steps, operations, constituent elements, and components, or a combination thereof in advance. In the specification, unless explicitly described to the contrary, the word "comprise" and variations such as "comprises" or "comprising", will be understood to imply the inclusion of stated elements but not the exclusion of any other elements.

Further, throughout the specification, when it is referred to as "planar", it means the case where a target part is viewed from above, and when it is referred to as "in cross-section", it means the case where a cross-section obtained by vertically cutting the target part is viewed from the side.

Further, throughout the specification, when it is referred to as "connected", this does not only mean that two or more constituent elements are directly connected, but may mean that two or more constituent elements are indirectly connected through another constituent element, are physically connected, electrically connected, or are integrated even though two or more constituent elements are referred as different names depending on a location and a function.

A sweat sensor patch according to the present disclosure may have a predetermined planar shape having an area to be attached to the skin, and may include, for example, a rectangular shape or an auxetic structure. According to the size, the form, the attachment location, the usage, and the like of the patch, a unit structure of the sweat sensor patch described below may be configured alone, or a plurality of unit structures may be distributed or arranged in the patch.

Figure 2:
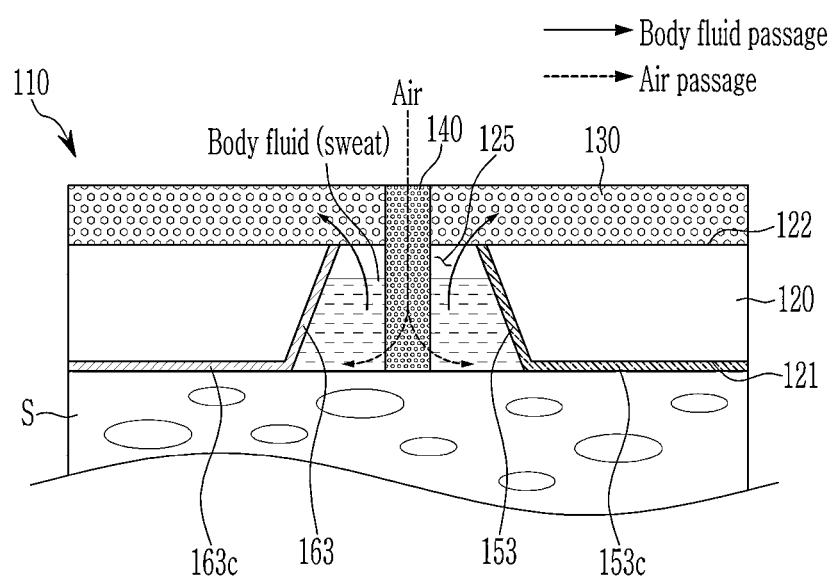
FIG. 2 is a cross-sectional view illustrating a combined unit structures of the sweat sensor patch illustrated in FIG. 1 taken along line II-II.

FIG. 1 is an exploded perspective view illustrating a unit structure of a sweat sensor patch according to an exemplary embodiment, and FIG. 2 is a cross-sectional view illustrating a combined unit structures of the sweat sensor patch illustrated in FIG. 1 taken along line II-II.

Referring to FIGS. 1 and 2, a sweat sensor patch 110 according to the present exemplary embodiment is a sensor patch that may be used by being attached to the skin S of a user, and includes an opening formed layer 120 including an opening 125 penetrating in a thickness direction, electrode layers 150 and 160 formed on an inner wall surface of the opening 125, and a porous layer 130 stacked on the opening formed layer 120. In the present exemplary embodiment, a porous pillar 140 connected with the porous layer 130 may be included in the opening 125 of the opening formed layer 120.

The opening formed layer 120 has a first surface 121 and a second surface 122 which face in opposite directions, and the opening 125 may penetrate from the first surface 121 to the second surface 122 in the thickness direction. Herein, the first surface 121 may be the surface attached to the skin S of the user, and the second surface 122 may be the surface facing the outside. Accordingly, the opening 125 may provide a passage through which sweat collected from the first surface 121 that is attached to the skin S is discharged to the second surface 122. The opening forming layer 120 may be made of a flexible material, for example, silicone, polymer, and resin, such as Poly(dimethylsiloxane) (PDMS) and Ecoflex®, which is not harmful to the human body and is bendable together with the skin.

In the present exemplary embodiment, the opening 125 may be configured to have a truncated cone shape whose diameter is decreased from the first surface 121 to the second surface 122. That is, the planar area of the cross-section of the opening 125 cut in a plane perpendicular to the thickness direction of the opening formed layer 120 may increase as being close to the first surface 121 and decreases as being close to the second surface 122. As described above, the diameter of the opening 125 decreases from the first surface 121 that is the entrance of the sweat to the second surface 122, so that a dead volume may be decreased.

The electrode layers 150 and 160 may be formed on the inner wall surface of the opening 125 to detect sweat. The electrode layers 150 and 160 may quantitatively or qualitatively collect data by measuring a flow rate or production rate of sweat, and ion concentration and components of sweat. For example, the electrode layers 150 and 160 may include silver nanowire (Ag NW), a nano-mesh electrode formed of a single wall carbon nanotube (SWNT) and the like, or a nano-mesh electrode plated with gold or a gold thin film.

The electrode layers 150 and 160 may include the working electrode 150 and the reference electrode 160 which forms a pair with the working electrode 150 and is electrically connected with the working electrode 150. The working electrode 150 may include a first working electrode 151 and a second working electrode 153, and the reference electrode 160 may include a first reference electrode 161 and a second reference electrode 163. The first working electrode 151 may be operated as a pair with the first reference electrode 161, and the second working electrode 153 may be operated as a pair with the second reference electrode 163. The number of pairs of the working electrode and the reference electrode may be two or more. For example, the working electrode 150 may include an ion selective electrode (ISE) formed by performing a surface treatment on an electrode.

The electrode layers 150 and 160 may be formed on the inner wall surface of the opening 125, and may be extended from the first surface 121 to the second surface 122. The first working electrode 151 and the second working electrode 153 forming the working electrode 150 may be formed while being spaced apart from each other with a gap at one side of the inner wall surface of the opening 125. The first reference electrode 161 and the second reference electrode 163 forming the reference electrode 160 may be formed while being spaced apart from each other with a gap at the other side of the inner wall surface of the opening 125. Accordingly, the electrode layers 150 and 160 may be provided in the form surrounded along the inner wall surface of the opening 125.

The porous layer 130 may be stacked on the second surface 122 of the opening formed layer 120, and be formed so as to cover the opening 125. The porous layer 130 may include a hydrophilic material, and thus has hydrophilicity. Due to the hydrophilic porous layer 130, the body fluid collected to the opening 125 may be guided to be more smoothly discharged to the second surface 122 of the opening formed layer 120. The porous layer 130 having the hydrophilicity may include, for example, carbon nanotube-poly(dimethylsiloxane) sponge (CNT-PDMS), a hydrophilic latex sponge, or a hydrophilic polyurethane sponge.

The porous pillar 140 may be formed so as to be extended in the thickness direction of the opening formed layer 120 in the opening 125. For example, the porous pillar 140 may be extended to penetrate from the first surface 121 of the opening formed layer 120 to the porous layer 130. Further, the porous pillar 140 is positioned while being spaced apart from the inner wall surface of the opening 125, and may be connected to and supported by the porous layer 130. In this case, the porous pillar 140 may include a hydrophobic material, for example, a PDMS sponge, and hydrophobically coated or treated polymer, resin, and silicone. Accordingly, outside air may flow into the opening 125 through the inner pores of the porous pillar 140, and the body fluid collected in the opening 125 may be discharged to the porous layer 130 having hydrophilicity around the porous pillar 140. Accordingly, an air passage and a body fluid passage may be implemented at the same time by the hydrophobic porous pillar 140 and the hydrophilic porous layer 130 in one opening 125.

The porous pillar 140 may be formed to have a cylindrical shape, and may also be configured to have either a truncated cone or an inverted truncated cone shape according to a change in the diameter of the porous pillar 140 in the longitudinal direction. For another example, the porous pillar 140 may also be formed of one of a polygonal prism, a polygonal truncated pyramid, and an inverted polygonal truncated pyramid.

Figure 3:
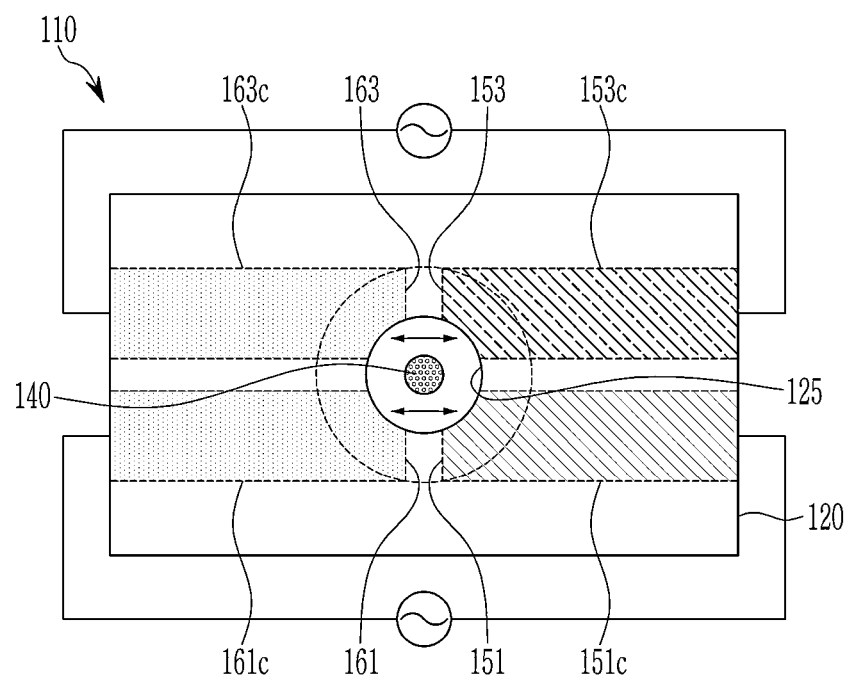
FIG. 3 is a top plan view illustrating a configuration in which the unit structures of the sweat sensor patch illustrated in FIG. 1 are combined and connected with an electrode.

FIG. 3 is a top plan view illustrating a configuration in which the unit structures of the sweat sensor patch illustrated in FIG. 1 are combined and connected with the electrode.

Referring to FIG. 3, the first working electrode 151 may be disposed to face the first reference electrode 161 at one side of the opening 125 and form a pair with the first reference electrode 161, and the second working electrode 153 may be disposed to face the second reference electrode 163 at one side of the opening 125 and form a pair with the second reference electrode 163. As described above, the working electrode 150 may be paired with the reference electrode 160 to measure impedance of the body fluid filled in the opening 125, and sense various information, such as a concentration, a flow rate, and a concentration of specific ions may be sensed according to various combinations of the working electrode 150. For example, the first working electrode 151 may be a $K^+$ ion selective electrode and the second working electrode 153 may be a $Na^+$ ion selective electrode.

The first working electrode 151, the second working electrode 153, the first reference electrode 161, and the second reference electrode 163 patterned on the inner wall surface of the opening 125 of the opening formed layer 120 may be connected to interconnection electrodes 151c, 153c, 161c, and 163c, which are extended from the first surface 121 of the opening formed layer 120 in one direction, respectively. The interconnection electrodes 151c, 153c, 161c, and 163c may be configured to be connected to an external sensing circuit, and connect the first working electrode 151 to the first reference electrode 161 and connect the second working electrode 153 to the second reference electrode 163.

Figure 4:
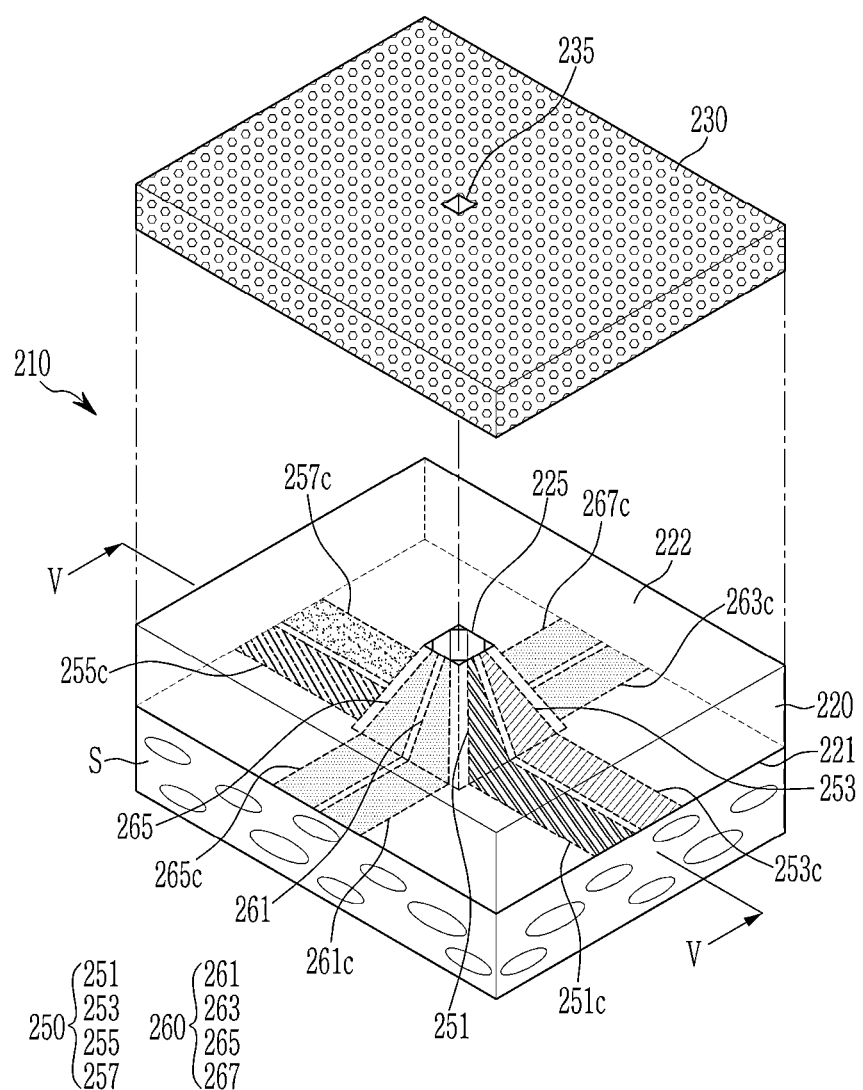
FIG. 4 is an exploded perspective view illustrating a unit structure of a sweat sensor patch according to another exemplary embodiment.
Figure 5:
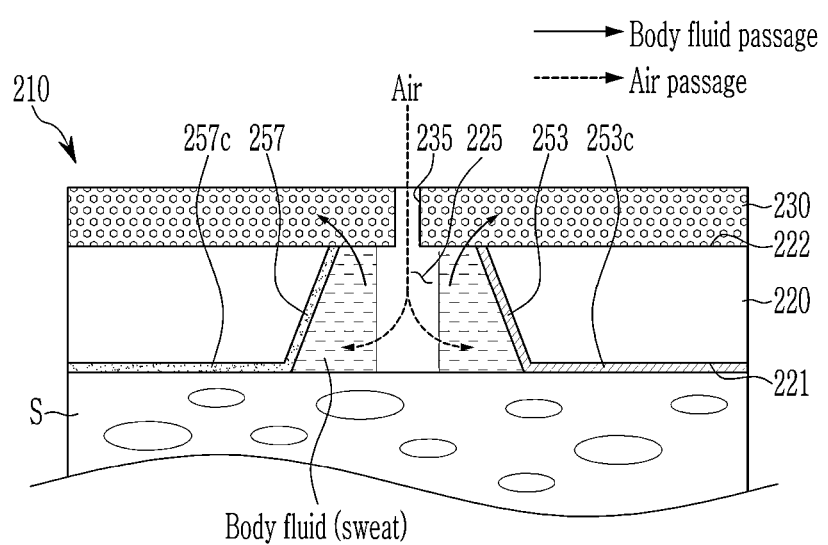
FIG. 5 is a cross-sectional view illustrating a combined unit structures of the sweat sensor patch illustrated in FIG. 4 taken along line V-V.

FIG. 4 is an exploded perspective view illustrating a unit structure of a sweat sensor patch according to another exemplary embodiment, and FIG. 5 is a cross-sectional view illustrating a combined unit structures of the sweat sensor patch illustrated in FIG. 4 taken along line V-V.

Referring to FIGS. 4 and 5, a sweat sensor patch 210 according to the present exemplary embodiment is a sensor patch that may be used by being attached to the skin S of a user, and includes an opening formed layer 220 including an opening 225 penetrating in a thickness direction, electrode layers 250 and 260 formed on an inner wall surface of the opening 225, and a porous layer 230 stacked on the opening formed layer 220. In the present exemplary embodiment, the porous layer 230 may have an air hole 235 penetrating so as to correspond to the opening 225.

The opening formed layer 220 has a first surface 221 and a second surface 222 which face in opposite directions, and the opening 225 may penetrate from the first surface 221 to the second surface 222 in the thickness direction. Herein, the first surface 221 may be the surface attached to the skin S of the user, and the second surface 222 may be the surface facing the outside. Accordingly, the opening 225 may provide a passage through which sweat collected from the first surface 221 that is attached to the skin S is discharged to the second surface 222.

In the present exemplary embodiment, a cross-section of the opening 225 cut in the plane perpendicular to the thickness direction of the opening formed layer 220 may be formed of a polygonal shape having corners. For example, the cross-section of the opening 225 may be rectangular, rectangular, or square. Further, the opening 225 may be configured such that the planar area of the cross-section becomes narrower from the first surface 221 to the second surface 222. As described above, the body fluid collected in the opening 225 having the corners may move to the porous layer 230 along the corners by surface tension.

The electrode layers 250 and 260 may be formed on the inner wall surface of the opening 225 to detect sweat. The electrode layers 250 and 260 may quantitatively or qualitatively collect data by measuring a flow rate or production rate of sweat, and ion concentration and components of sweat. For example, the electrode layers 250 and 260 may include silver nanowire (Ag NW), a nano-mesh electrode formed of a single wall carbon nanotube (SWNT) and the like, or a nano-mesh electrode plated with gold or a gold thin film.

The electrode layers 250 and 260 may include the working electrode 250 and the reference electrode 260 which forms a pair with the working electrode 250 and is electrically connected with the working electrode 250. The working electrode 250 may include a first working electrode 251, a second working electrode 253, a third working electrode 255, and a fourth working electrode 257, and the reference electrode 260 may include a first reference electrode 261, a second reference electrode 263, a third reference electrode 265, and a fourth reference electrode 267. For example, the working electrode 250 may include an ion selective electrode (ISE) formed by performing a surface treatment on an electrode.

The electrode layers 250 and 260 may be formed on the inner wall surface of the opening 225, and extended from the first surface 221 to the second surface 222. The first working electrode 251 and the second working electrode 253 may be formed while being spaced apart from each other with a gap at one side of the inner wall surface of the opening 225, and the third working electrode 255 and the fourth working electrode 257 may be formed while being spaced apart from each other with a gap at the other side of the inner wall surface of the opening 225. In this case, the first working electrode 251 and the second working electrode 253, and the third working electrode 255 and the fourth working electrode 257 may be disposed on the inner wall surfaces of the opening 225 facing each other.

The reference electrode 260 may be disposed on the inner wall surface of the opening 225 on which the working electrode 250 is not formed on the inner wall surface. Accordingly, the first reference electrode 261 and the second reference electrode 263 may be formed while being spaced apart from each other with a gap at one side of the inner wall surface of the opening 225, and the third reference electrode 265 and the fourth reference electrode 267 may be formed while being spaced apart from each other with a gap at the other side of the inner wall surface of the opening 225. In this case, the first reference electrode 261 and the second reference electrode 263, and the third reference electrode 265 and the fourth reference electrode 267 may be disposed on the inner wall surfaces of the opening 225 facing each other.

The porous layer 230 may be stacked on the second surface 222 of the opening formed layer 220, and have the air hole 235 penetrating so as to correspond to the opening 225. A planar area of the air hole 235 of the porous layer 230 may be smaller than a minimum planar area of the opening 225 of the opening formed layer 220. Outside air may flow into the opening 225 through the air hole 235.

Further, the porous layer 130 may include a hydrophilic material, and thus has hydrophilicity. Due to the hydrophilic porous layer 230, the body fluid collected to the opening 225 may be guided to be more smoothly discharged to the second surface 222 of the opening formed layer 220. That is, the body fluid filled in the opening 225 may be absorbed by the hydrophilic material of the porous layer 230 in the upper portion and then removed through evaporation.

Figure 6:
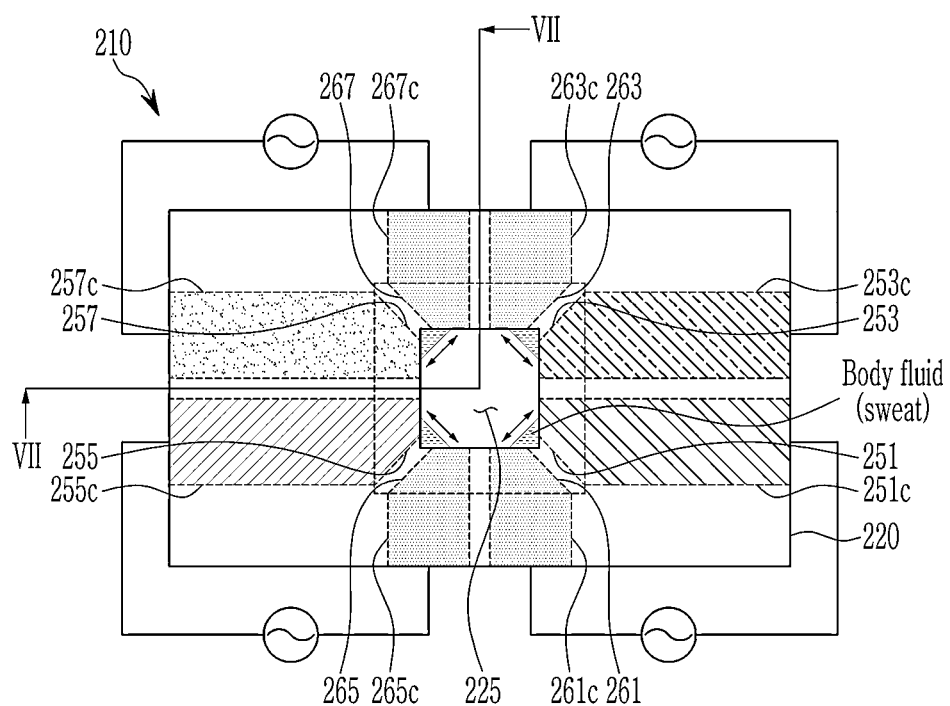
FIG. 6 is a top plan view illustrating a configuration in which the unit structures of the sweat sensor patch illustrated in FIG. 4 are combined and connected with an electrode.
Figure 7:
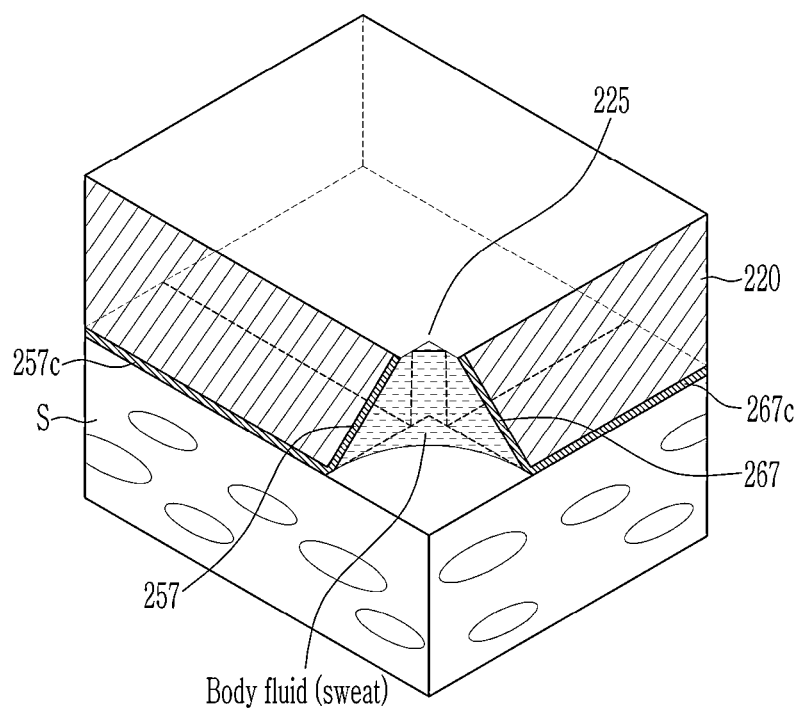
FIG. 7 is a cut perspective view illustrating the unit structure of the sweat sensor patch illustrated in FIG. 6 taken along line VII-VII.

FIG. 6 is a top plan view illustrating a configuration in which the unit structures of the sweat sensor patch illustrated in FIG. 4 are combined and connected with the electrode, and FIG. 7 is a cut perspective view illustrating the unit structure of the sweat sensor patch illustrated in FIG. 6 taken along line VII-VII.

Referring to FIG. 6, the first working electrode 251 may be disposed to be adjacent to the first reference electrode 261 with one corner of the opening 225 interposed therebetween and form a pair with the first reference electrode 261, and the second working electrode 253 may be disposed to be adjacent to the second reference electrode 263 with one corner of the opening 225 interposed therebetween and form a pair with the second reference electrode 263. Similarly, the third working electrode 255 may be disposed to be adjacent to the third reference electrode 265 with one corner of the opening 225 interposed therebetween and form a pair with the third reference electrode 265, and the fourth working electrode 257 may be disposed to be adjacent to the fourth reference electrode 267 with one corner of the opening 225 interposed therebetween and form a pair with the fourth reference electrode 267. As described above, the working electrode 250 may be paired with the reference electrode 260 to measure impedance of the body fluid filled in the opening 225, and sense various information, such as a concentration, a flow rate, and a concentration of specific ions may be sensed according to various combinations of the working electrode 250. For example, the first working electrode 251 may be a $Cl^-$ ion selective electrode, the second working electrode 253 may be a $Na^+$ ion selective electrode, and the third working electrode 255 may be a $K^+$ ion selective electrode. Further, the fourth working electrode 257 may be another working electrode (WE).

The first working electrode 251, the second working electrode 253, the third working electrode 255, and the fourth working electrode 257 patterned on the inner wall surface of the opening 225 of the opening formed layer 220 may be connected to interconnection electrodes 251c, 253c, 255c, and 257c, which are extended from the first surface 221 of the opening formed layer 220 in one direction, respectively. Further, the first reference electrode 261, the second reference electrode 263, the third reference electrode 265, and the fourth reference electrode 267 may be connected to interconnection electrodes 261c, 263c, 265c, and 267c, which are extended from the first surface 221 of the opening formed layer 220 in one direction, respectively. The interconnection electrodes 251c, 253c, 255c, 257c, 261c, 263c, 265c, and 267c may be connected to an external sensing circuit to connect the first working electrode 251 to the first reference electrode 261, connect the second working electrode 253 to the second reference electrode 263, connect the third working electrode 255 to the third reference electrode 265, and connect the fourth working electrode 257 to the fourth reference electrode 267.

Referring to FIG. 7, the body fluid (sweat) may ascend from the first surface 221 to the second surface 222 along the corner by capillary phenomenon according to surface tension at the corner portion of the opening 225. In this case, the body fluid (sweat) is in contact with the working electrodes and the reference electrodes which are adjacent to each other with the respective corners, so that component information of the body fluid (sweat) may be sensed. When the cross-section of the opening 225 is rectangular, for example, four pairs of working electrodes and reference electrodes may be selected and combined to selectively measure the concentration of specific ions.

Figure 8:
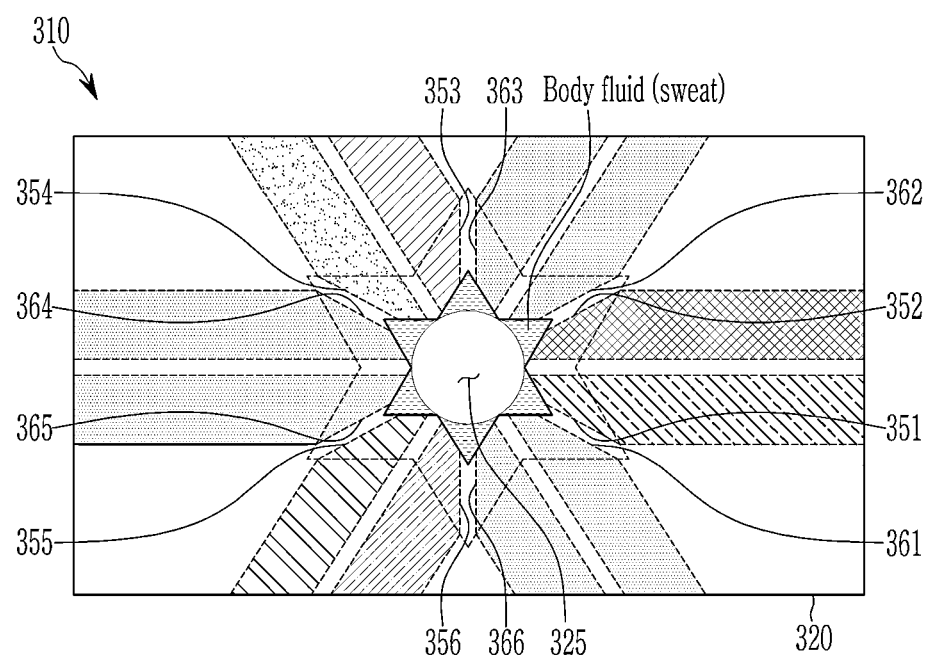
FIG. 8 is a top plan view illustrating a unit structure of a sweat sensor patch according to a still another exemplary embodiment.

FIG. 8 is a top plan view illustrating a unit structure of a sweat sensor patch according to a still another exemplary embodiment.

Referring to FIG. 8, a sweat sensor patch 310 according to the present exemplary embodiment includes an opening formed layer 320 including an opening 325 penetrating in a thickness direction, and electrode layers 350 and 360 formed on an inner wall surface of the opening 325 similar to the sweat sensor patch illustrated in FIG. 4. A porous layer (not illustrated) may be stacked on the opening formed layer 320, and the porous layer may have an air hole penetrating so as to correspond to the opening 325.

In the present exemplary embodiment, a cross-section of the opening 325 may have a hexagram shape, and thus, the opening 325 may have six protruding corners and six concave corners. The opening 325 may be configured such that a planar area of the cross-section becomes narrower from the surface attached to the skin to the surface facing the outside. As described above, the body fluid collected in the opening 325 having the corners may move to the porous layer along the concave corners by surface tension.

The electrode layers 350 and 360 may be formed on the inner wall surface of the opening 325 to detect sweat components. The electrode layers 350 and 360 may include the working electrode 350 and the reference electrode 360 which makes a pair with the working electrode 350 and is connected with the working electrode 350. The working electrode 350 may include a first working electrode 351, a second working electrode 352, a third working electrode 353, a fourth working electrode 354, a fifth working electrode 355, and a sixth working electrode 356. The reference electrode 360 may include a first reference electrode 361, a second reference electrode 362, a third reference electrode 363, a fourth reference electrode 364, a fifth reference electrode 365, and a sixth reference electrode 366.

The first working electrode 351 may be disposed to be adjacent to the first reference electrode 361 with one concave corner of the opening 325 interposed therebetween and form a pair with the first reference electrode 361, and the second working electrode 352 may be disposed to be adjacent to the second reference electrode 362 with another concave corner of the opening 325 interposed therebetween and form a pair with the second reference electrode 362. Further, the third working electrode 353 may be disposed to be adjacent to the third reference electrode 363 with another corner of the opening 325 interposed therebetween and form a pair with the third reference electrode 363, and the fourth working electrode 354 may be disposed to be adjacent to the fourth reference electrode 364 with another corner of the opening 325 interposed therebetween and form a pair with the fourth reference electrode 364. Similarly, the fifth working electrode 355 may be disposed to be adjacent to the fifth reference electrode 365 with another corner of the opening 325 interposed therebetween and form a pair with the fifth reference electrode 365, and the sixth working electrode 356 may be disposed to be adjacent to the sixth reference electrode 366 with another corner of the opening 325 interposed therebetween and form a pair with the sixth reference electrode 366.

As described above, the working electrode 350 may be paired with the reference electrode 360 to measure impedance of the body fluid filled in the opening 325, and sense various information, such as a concentration, a flow rate, and a concentration of specific ion may be sensed according to various combinations of the working electrode 350. It is possible to add the type of sensible information by applying an ion selective electrode that selectively measures a concentration of specific ions to the electrode of each electrode pair.

Figure 9:
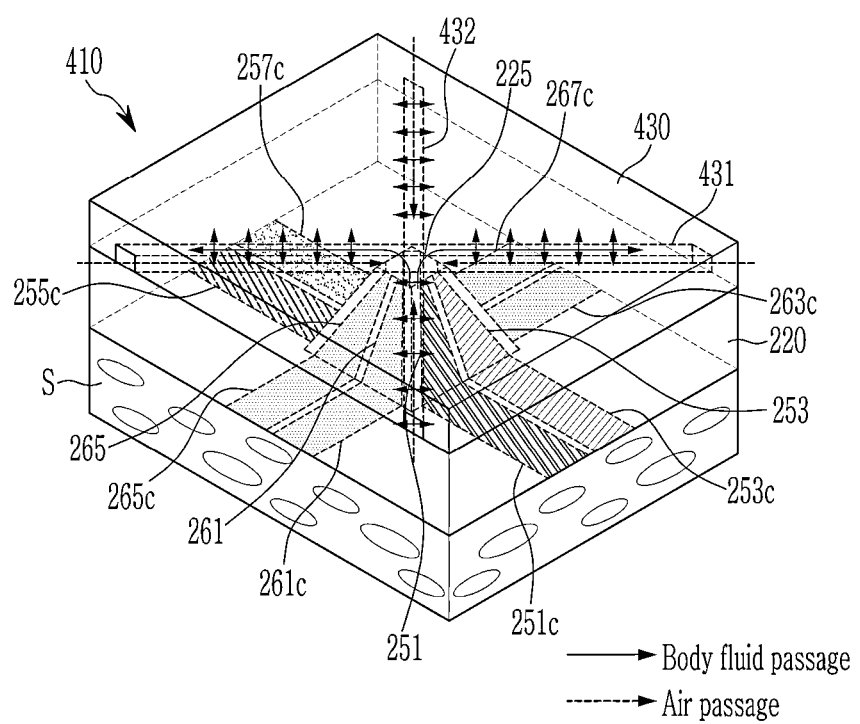
FIG. 9 is a perspective view illustrating the unit structure of the sweat sensor patch according to still another exemplary embodiment.

FIG. 9 is a perspective view illustrating the unit structure of the sweat sensor patch according to still another exemplary embodiment.

Referring to FIG. 9, a sweat sensor patch 410 according to the present exemplary embodiment includes an opening formed layer 220 including an opening 225 penetrating in a thickness direction, and electrode layers 250 and 260 formed on an inner wall surface of the opening 225 similar to the sweat sensor patch illustrated in FIG. 4. In the present exemplary embodiment, a channel formed layer 430 is stacked on the opening formed layer 220, and the channel formed layer 430 may include air channels 431 and 432 extending in a planar direction of the opening formed layer 220.

For example, the channel formed layer 430 may be made of a hydrophilic material, such as hydrogel, or a hygroscopic material, or may include a porous layer including a hydrophilic material.

The opening formed layer 220 has a first surface 221 and a second surface 222 which face in opposite directions, and the opening 225 may penetrate from the first surface 221 to the second surface 222 in the thickness direction. In the present exemplary embodiment, a cross-section of the opening 225 cut in the plane perpendicular to the thickness direction of the opening formed layer 220 may be formed of a polygonal shape having corners. As described above, the body fluid collected in the opening 225 having the corners may move to the channel formed layer 430 along the corners by surface tension.

The electrode layers 250 and 260 may be formed on the inner wall surface of the opening 225 to detect sweat components. The electrode layers 250 and 260 may include the working electrode 250 and the reference electrode 260 which forms a pair with the working electrode 250 and is electrically connected with the working electrode 250. The electrode layers 250 and 260 may be formed on the inner wall surface of the opening 225, and extended from the first surface 221 to the second surface 222. As described above, the working electrode 250 may be paired with the reference electrode 260 to measure impedance of the body fluid filled in the opening 225, and sense various information, such as a concentration, a flow rate, and a concentration of specific ions may be sensed according to various combinations of the working electrode 250.

The more detailed structures of the opening formed layer 220 and the electrode layers 250 and 260 may be implemented similar to the sweat sensor patch of the exemplary embodiment illustrated in FIG. 4, so that the detailed description thereof will be omitted.

Figure 10:
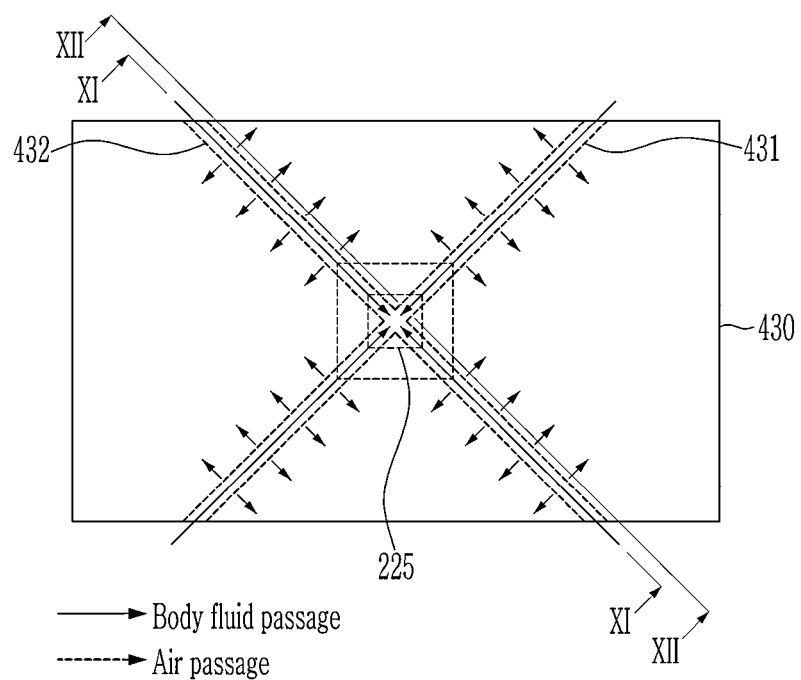
FIG. 10 is a top plan view illustrating the unit structure of the sweat sensor patch illustrated in FIG. 9.
Figure 11:
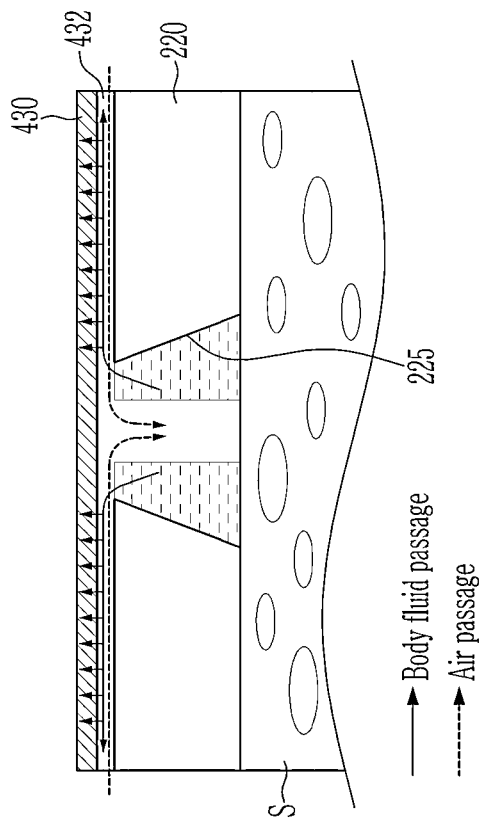
FIG. 11 is a cross-sectional view illustrating the unit structure of the sweat sensor patch illustrated in FIG. 10 taken along line XI-XI.
Figure 12:
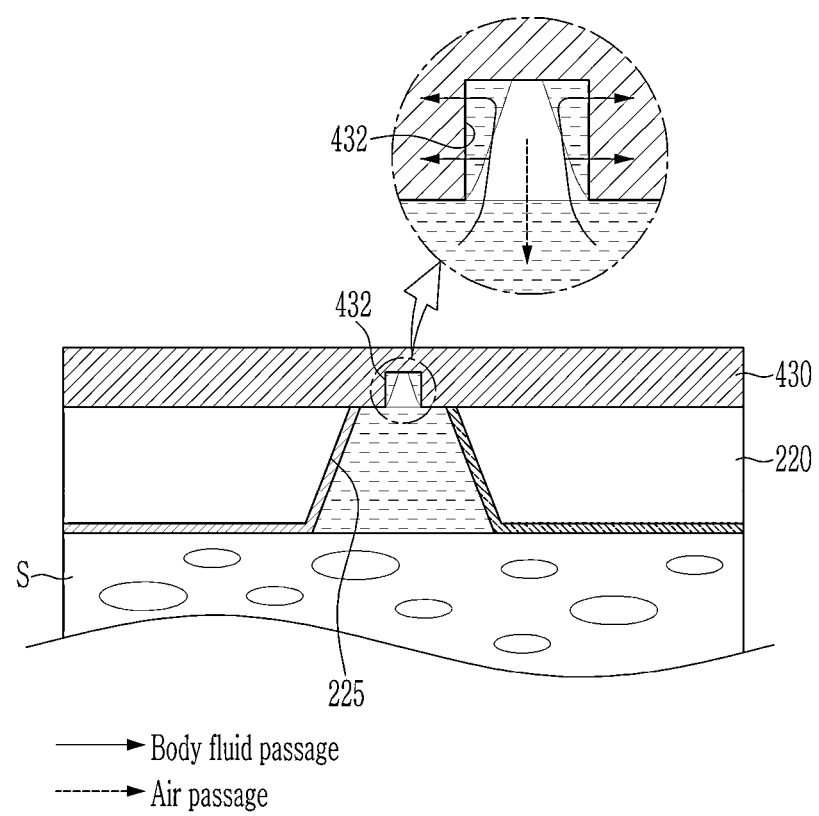
FIG. 12 is a cross-sectional view illustrating the unit structure of the sweat sensor patch illustrated in FIG. 10 taken along line XII-XII.

FIG. 10 is a top plan view illustrating the unit structure of the sweat sensor patch illustrated in FIG. 9, FIG. 11 is a cross-sectional view illustrating the unit structure of the sweat sensor patch illustrated in FIG. 10 taken along line XI-XI, and FIG. 12 is a cross-sectional view illustrating the unit structure of the sweat sensor patch illustrated in FIG. 10 taken along line XII-XII.

Referring to FIG. 10, the channel formed layer 430 may be stacked on the second surface 222 of the opening formed layer 220, and be formed to cover the opening 225. The air channels 431 and 432 formed in the channel formed layer 430 may be configured so as to pass through the opening 225 formed in the opening formed layer 220, and may be extended at least in four directions about the opening 225 in a plane. Accordingly, the air channels 431 and 432 may form a space between the second surface 222 of the opening formed layer 220 and the channel formed layer 430, and be configured to communicate with the opening 225. Further, the air channels 431 and 432 may have a structure in which the air channels 431 and 432 may extend to a border of the sweat sensor patch 410, that is, a border of the channel formed layer 430, so that end portions of the air channels 431 and 432 are opened (open-end structure).

Referring to FIGS. 11 and 12, the body fluid that is collected in the opening 225 and discharged may move along the inner wall surfaces of the air channels 431 and 432 of the channel formed layer 430 and simultaneously be absorbed even in the channel formed layer 430 made of the hydrophilic or hygroscopic material. Accordingly, through the air channels 431 and 432 of the channel formed layer 430, an air passage into which outside air flows and a body fluid passage through which the body fluid moves may be simultaneously implemented in a separate form. As a result, compared to the inner side of the channel is made of a hydrophobic material, the body fluid in the channel may be quickly and easily removed. Herein, when the absorption rate of the hydrophilic/hygroscopic material is fast, the mechanism in which the body fluid is removed through the absorption may prevail, and when the absorption rate is slow, the mechanism in which the body fluid is slowly absorbed while flowing along the channels may prevail.

Figure 13:
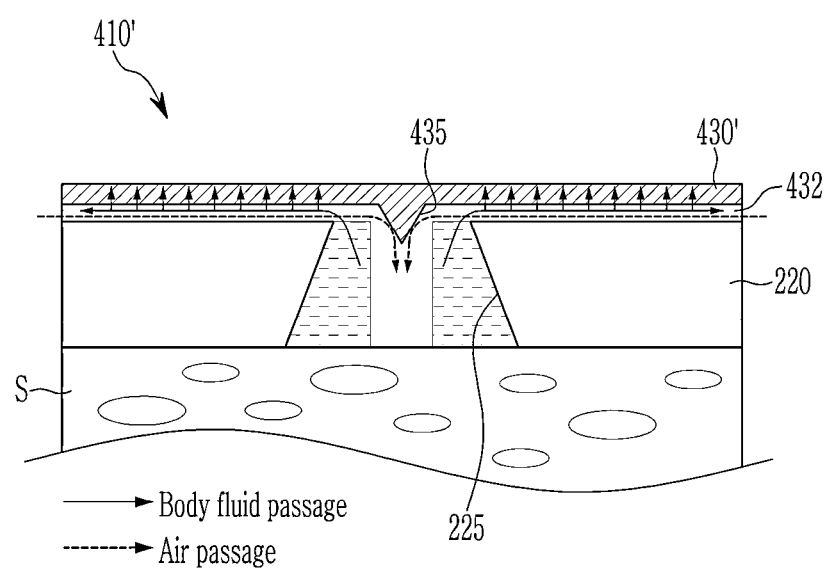
FIG. 13 is a cross-sectional view illustrating another modified example of the exemplary embodiment illustrated in FIG. 9.

FIG. 13 is a cross-sectional view illustrating another modified example of the exemplary embodiment illustrated in FIG. 9, and is a cross-sectional view taken along line a cutting line at the same position as that of the cutting line of FIG. 11.

Referring to FIG. 13, a sweat sensor patch 410' according to the present modified example includes the sweat sensor patch 410 illustrated in FIG. 9 as the basic structure, and may further include a pillar 435 formed at a position corresponding to an opening 225 in a channel formed layer 430'. The pillar 435 may extend from a surface in a thickness direction of an opening formed layer 220 toward the opening 225 from the surface where the channel formed layer 430' faces the opening formed layer 220. The pillar 435 may have a height such that an end of the pillar 435 extends to be partially received into the opening 225. Further, the pillar 435 may be formed of a cone or polygonal pyramid (triangular pyramid, quadrangular pyramid, and the like) so that the end of the pillar 435 has a pointed shape, and may be made of the same material as that of the channel formed layer 430'. For another example, the pillar 435 may also be formed to have a shape of a cylinder, a truncated cone, an inverted truncated cone, a polygonal prism, a polygonal truncated pyramid, or an inverted polygonal truncated cone.

Figure 14:
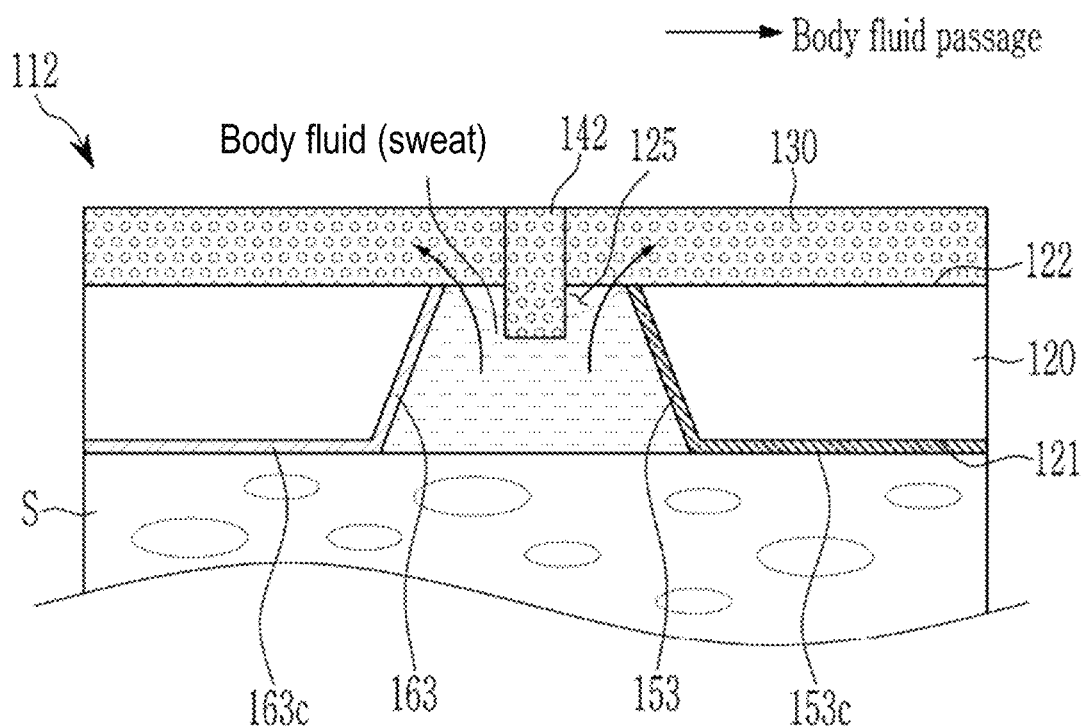
FIG. 14 is a cross-sectional view illustrating a unit structure of a sweat sensor patch according to yet another exemplary embodiment.

FIG. 14 is a cross-sectional view illustrating a unit structure of a sweat sensor patch according to yet another exemplary embodiment.

Referring to FIG. 14, a sweat sensor patch 112 according to the present exemplary embodiment includes a porous pillar 132 that is shorter than the porous pillar 140 of the sweat sensor patch 110 illustrated in FIG. 2. In the present exemplary embodiment, the porous pillar 132 is supported while being connected to a porous layer 130, and the porous pillar 132 extends from the porous layer 130 in the thickness direction of an opening formed layer 120 so that an end of the porous pillar 132 is partially received in the opening 125, and may be positioned while being spaced apart from a first surface 121 of the opening formed layer 120. In this case, the porous pillar 132 may be the extension of the hydrophilic porous layer 130, and thus, the porous pillar 132 may include a hydrophilic material.

Hereinafter, the process of manufacturing the sweat sensor patch, and the result of the evaluation of a sweat clearance characteristic by using the manufactured sweat sensor patch will be described in more detail through an illustrative example. However, it should be noted that the protection scope of the present invention is not intended to be limited to the following example.

(Manufacture Sweat Sensor Patch)

Example 1. Sweat Sensor Patch Having Porous Layer (CNT-PDMS Sponge)

Figure 15:
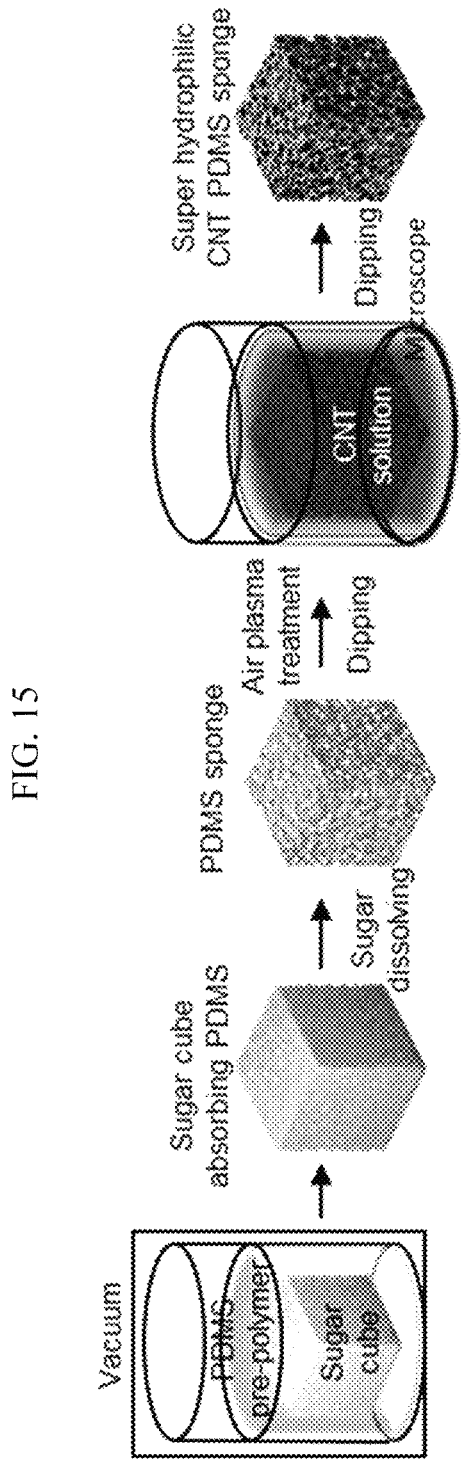
FIG. 15 is a process diagram illustrating a CNT-PDMS sponge (porous layer) manufacturing process.

A PDMS sponge was manufactured by putting a sugar cube into a vacuum pump in the state where the sugar cube was dipped in a solution in which PDMS and a curing agent were mixed at a ratio of 10:1 and absorbing the sugar cube in the solution, baking the sugar cube in the oven at 65 degrees for 2 hours, and dissolving sugar with hot water, followed by drying. A CNT-PDMS sponge (porous layer) was manufactured by soaking the manufactured PDMS sponge in a CNT dispersion solution and then drying the PDMS sponge (see FIG. 15).

Figure 16:
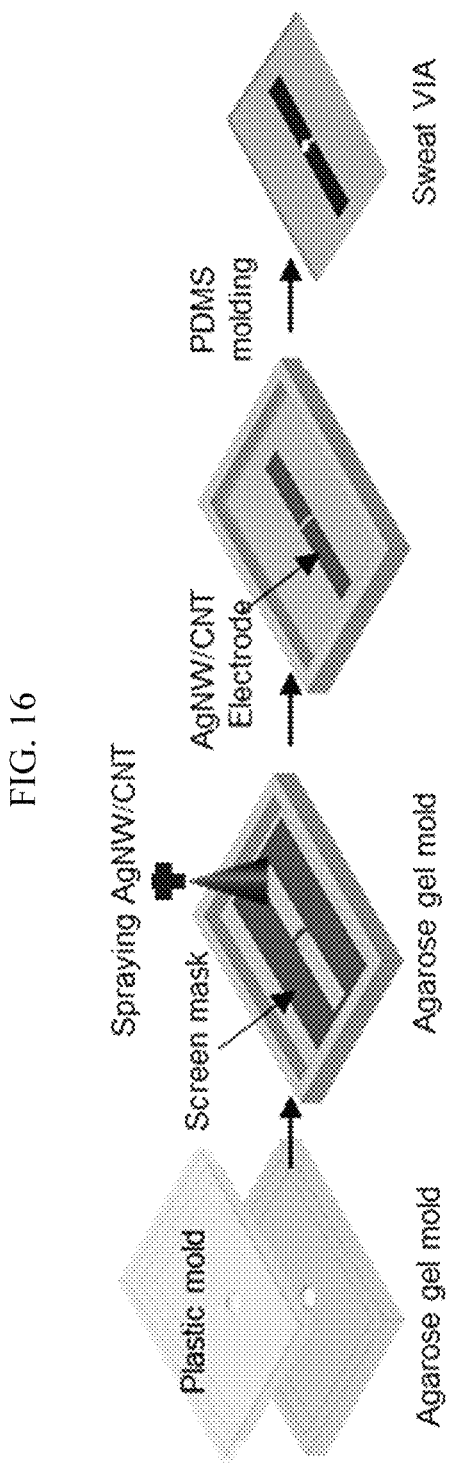
FIG. 16 is a process diagram illustrating an opening formed layer (sweat VIA) manufacturing process.

An agarose gel mold was manufactured by dissolving an agarose aqueous solution with a microwave, pouring the dissolved agarose aqueous solution in an acryl mold including a pattern formed with a sweat VIA, curing the agarose aqueous solution at room temperature for 2 hours, and then removing the cured layer from the mold. After the cured agarose gel mold was covered with a screen mask in the form of an electrode, an electrode was formed by spraying AgNW and a CNT solution. A sweat VIA (opening formed layer) was manufactured by removing the screen mask, and then curing the agarose gel mold formed with the electrode in the oven by pouring a mixed solution of PDMS and the curing agent and then removing the agarose gel mold (see FIG. 16).

Further, the sweat sensor patch element was manufactured by applying the PDMS to the sweat VIA (height 1 mm) and attaching the CNT-PDMS sponge by applying heat.

Example 2. Sweat Sensor Patch Including a Hydrogel Layer (Channel Formed Layer) Having an Open-End Channel An agarose (Bioline company) aqueous solution was prepared at a concentration of 5 w/v %, dissolved with microwave, and then poured into an acryl mold including a pattern for forming a channel, and cured at room temperature for 2 hours. Then, a hydrogel layer having an open-end channel was manufactured by removing the cured layer from the mold.

The sweat sensor patch was manufactured by attaching the manufactured hydrogel layer (channel formed layer) having the open-end channel to the sweat VIA (height 0.5 mm) manufactured in Example 1 by applying the PDMS and applying heat to the sweat VIA.

Evaluation Example

1. Evaluation of Sweat Clearance Characteristic of Example 1

Figure 17:
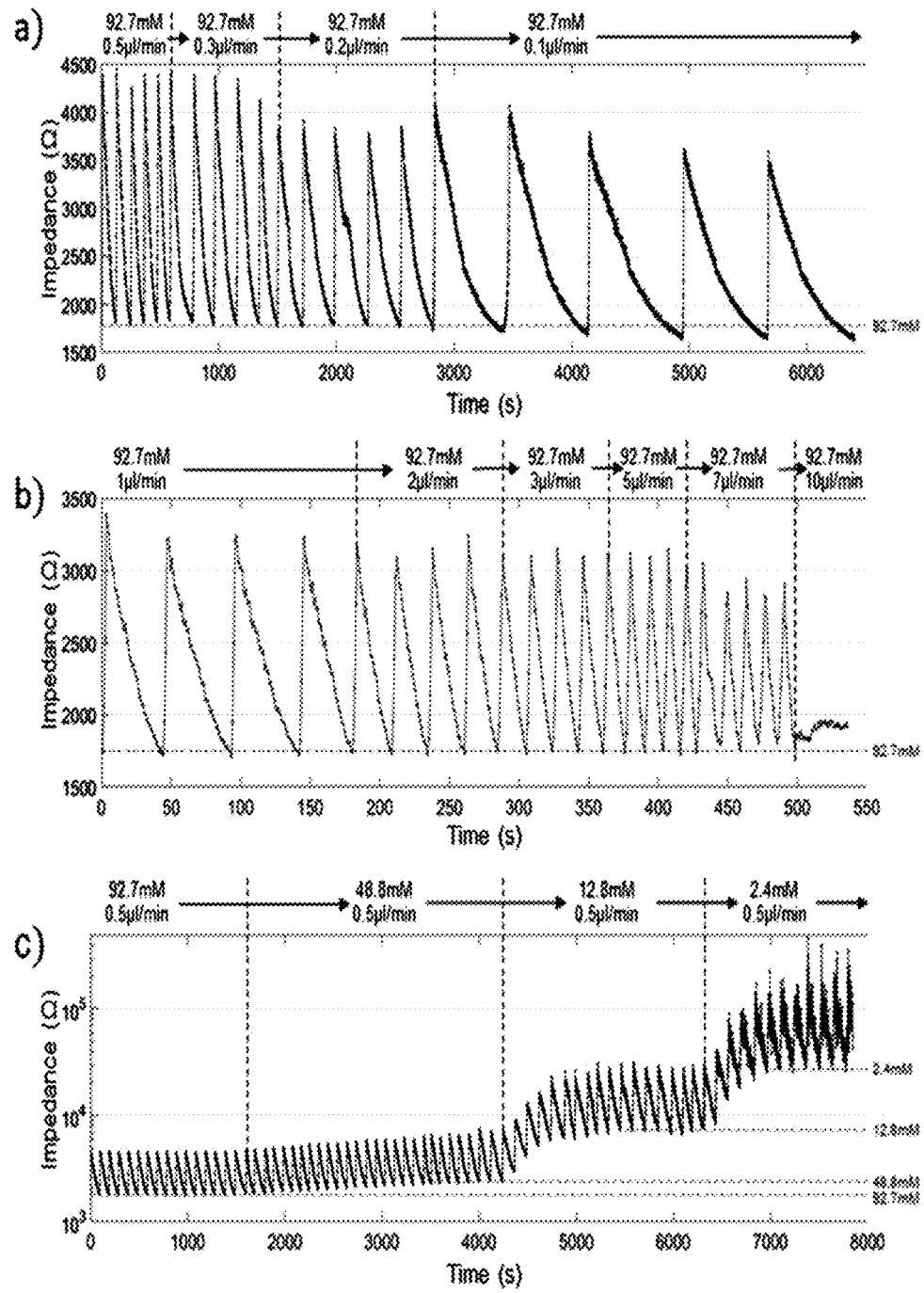
FIG. 17 is a graph illustrating an evaluation of a sweat clearance characteristic of the sweat sensor patch in which the CNT-PDMS sponge (porous layer) is attached to the opening formed layer (sweat VIA).

A sweat clearance characteristic was evaluated for the sweat sensor patch manufactured in Example 1. Impedance of the sweat VIA was measured by injecting NaCl solutions of various concentrations (2.4 to 93 mM) into the sweat VIA while changing the injection rate (0.5 to 10 μL/min) through a syringe pump. The measurement result is represented in FIG. 17. (a) and (b) of FIG. 17 are the graphs representing the sweat clearance characteristic according to a change in a flow rate, and (c) of FIG. 17 is a graph representing the result of the evaluation of the sweat clearance characteristic according to a change in a concentration of ions. As represented in FIG. 17, it can be seen that the impedance gradually decreases as the solution is filled to a certain volume even without external intervention, and then impedance rises sharply as sweat clearance occurs, and it can be seen that the cycle, in which as the solution fills again, the impedance gradually decreases, and the impedance increases after clearance, is repeated. Through this, it can be confirmed that sweat clearance occurs well.

2. Evaluation of Sweat Clearance Characteristic of Example 2

Figure 18:
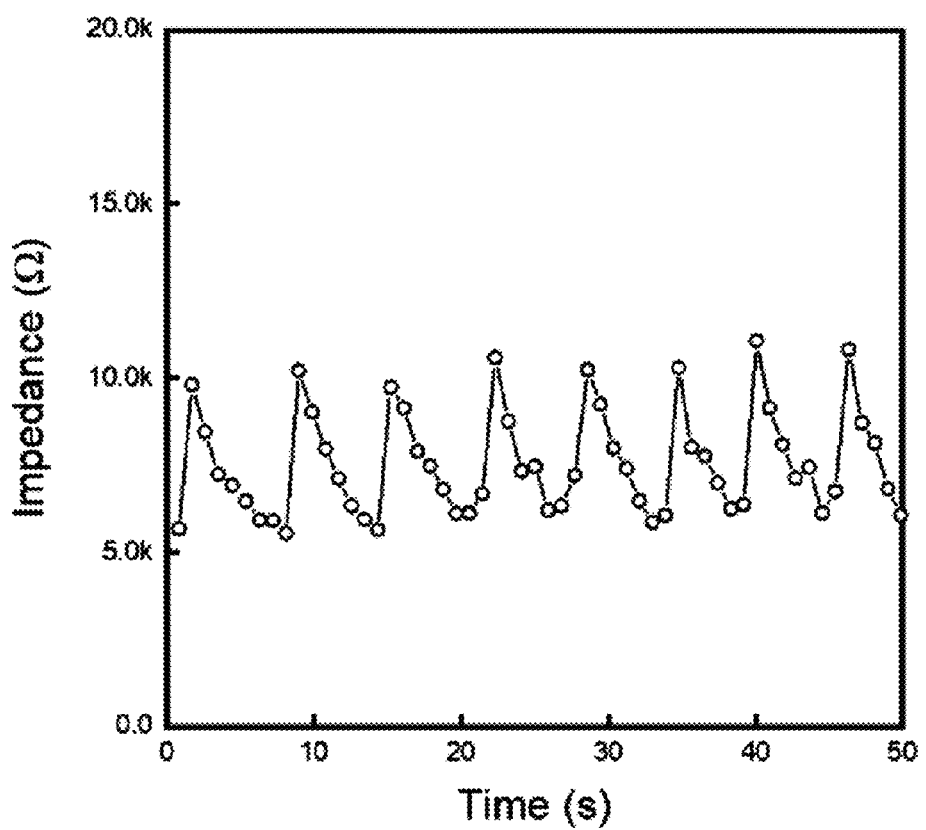
FIG. 18 is a graph illustrating an evaluation of a sweat clearance characteristic of the sweat sensor patch in which a hydrogel layer including an open-end channel is attached to the opening formed layer (sweat VIA).

A sweat clearance characteristic was evaluated for the sweat sensor patch manufactured in Example 2. Impedance of the sweat VIA was measured while injecting an NaCl solution of 100 mM into the sweat VIA through a syringe pump in a speed of 2 μL/min. The measurement result is represented in FIG. 18. As represented in FIG. 18, it can be seen that the impedance gradually decreases as the solution is filled to a certain volume, and then impedance rises sharply as sweat clearance occurs, and it can be seen that the cycle, in which as the solution fills again, the impedance gradually decreases, and the impedance increases after clearance, is repeated. Through this, it can be confirmed that sweat clearance occurs well.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

DESCRIPTION OF SYMBOLS 110, 210, 310, 410: Sweat sensor patch
120, 220, 320: Opening formed layer 121, 221: First surface
122, 222: Second surface
125, 225, 325: Opening
130, 230: Porous layer
140: Porous pillar
150, 160, 250, 260, 350, 360: Electrode layer
151, 251, 351: First working electrode
153, 253, 352: Second working electrode
161, 261: First reference electrode
163, 263: Second reference electrode
235: Air hole
255, 353: Third working electrode
257, 354: Fourth working electrode
265: Third reference electrode
267: Fourth reference electrode
430: Channel formed layer
431, 432: Air channel

What is claimed is:

1. A sweat sensor patch configured to be attached to a skin of a user and used, the sweat sensor patch comprising:
an opening formed layer which has a first surface and a second surface which face in opposite directions, and includes an opening penetrating in a thickness direction from the first surface to the second surface;
an electrode layer formed on an inner wall surface of the opening;
a porous layer which is stacked on the second surface of the opening formed layer and is formed to cover the opening; and
a porous pillar which extends in the thickness direction of the opening formed layer within the opening and is connected with the porous layer,
wherein the porous pillar includes a hydrophobic material.

2. The sweat sensor patch of claim 1, wherein:
the porous layer includes a hydrophilic material.

3. The sweat sensor patch of claim 1, wherein:
the porous pillar is positioned to be spaced apart from the inner wall surface of the opening.

4. The sweat sensor patch of claim 1, wherein:
the porous pillar is fixed to and supported by the porous layer.

5. The sweat sensor patch of claim 1, wherein:
the porous pillar extends so as to penetrate the porous layer from the first surface of the opening formed layer.

6. The sweat sensor patch of claim 1, wherein:
the porous pillar is spaced from the first surface of the opening formed layer, so that one end of the porous pillar is positioned within the opening.

7. The sweat sensor patch of claim 6, wherein:
the porous layer and the porous pillar include a hydrophilic material.

8. The sweat sensor patch of claim 1, wherein:
the electrode layer includes a working electrode and a reference electrode which forms a pair with the working electrode and is electrically connected with the working electrode.

9. A sweat sensor patch configured to be attached to a skin of a user and used, the sweat sensor patch comprising:
an opening formed layer which has a first surface and a second surface which face in opposite directions, and includes an opening penetrating in a thickness direction from the first surface to the second surface;
an electrode layer formed on an inner wall surface of the opening;
a channel formed layer which is stacked on the second surface of the opening formed layer; and
an air channel defined at least in part by the channel formed layer that communicates with the opening and extending in a plane direction of the opening formed layer,
wherein the plane direction is parallel to the second surface, and
wherein the air channel extends entirely between opposite ends of the channel formed layer in the plane direction.

10. The sweat sensor patch of claim 9, wherein:
the air channel extends at least in four directions about the opening in the plane direction of the opening formed layer.

11. The sweat sensor patch of claim 9, wherein:
the air channel is formed in a space between the second surface of the opening formed layer and the channel formed layer.

12. The sweat sensor patch of claim 9, wherein:
the channel formed layer further includes a pillar extending in a thickness direction of the channel formed layer from a surface facing the opening formed layer at a position corresponding to the opening.

13. The sweat sensor patch of claim 9, wherein:
the channel formed layer includes a hydrophilic material, a hygroscopic material, or a hydrogel.

14. The sweat sensor patch of claim 9, wherein:
a cross-section of the opening cut in a plane perpendicular to the thickness direction of the opening formed layer is formed of a polygon having corners.

15. The sweat sensor patch of claim 9, wherein:
the electrode layer includes a working electrode and a reference electrode which forms a pair with the working electrode and is electrically connected with the working electrode, and
the working electrode is disposed to be adjacent to the reference electrode with one corner of the opening interposed therebetween to form the pair with the reference electrode.

* * * * *